United States Patent [19]

Ernst

[11] 4,444,045
[45] Apr. 24, 1984

[54] HAND-OPERATED HARDNESS METER

[76] Inventor: Alfred Ernst, Via San Martino 6, 6943 Vezia Ticino, Switzerland

[21] Appl. No.: 357,559

[22] Filed: Mar. 12, 1982

[30] Foreign Application Priority Data

Apr. 22, 1981 [CH] Switzerland .......................... 2639/81

[51] Int. Cl.³ ............................................. G01N 3/48
[52] U.S. Cl. ....................................................... 73/82
[58] Field of Search ................... 73/78, 79, 81, 83, 85

[56] References Cited

U.S. PATENT DOCUMENTS 1,708,262  4/1929  Davis et al. .
3,879,982  4/1975  Schmidt .
4,034,603  7/1977  Leeb et al. .

FOREIGN PATENT DOCUMENTS 1115106  5/1968  United Kingdom ..................... 73/82

*Primary Examiner*—S. Clement Swisher
*Attorney, Agent, or Firm*—Michael J. Striker

[57] ABSTRACT

The hardness meter is so designed as to render the applied measurement load independent from the force that the operator is capable to exhert and as to provide an instantaneous load permitting a precise measure even if the equipment is shifted during the operation. Such hardness meter includes, between the mobile structure operated by the user's hands and the penetrating pin, a device capable of exherting an instantaneous force on the penetrating pin.

This device is formed by a plated spring (49) carried by an inertia mass (45) sliding along the guiding columns (10 and 11) and presenting a convexity which may be released from one side to the other of the median plane; when it is arranged on one side of the plane it is loaded and when it turns to the other side provides the instantaneous force which throws along said columns the inertial mass braked, however by friction means (50, 51 and 52) thus preventing the discharge of the reaction forces against the operator's hands.

10 Claims, 9 Drawing Figures

HAND-OPERATED HARDNESS METER

The present invention refers to a hand-operated portable hardness meter.

Hand-operated portable hardness meters are already known. They are normally of the pre-load and load type. In these hardness meters the applied load is imposed by the operator's hands, causing the controlled compression of a spring by means of which a constant load is exherted on the penetrating pin.

A first inconvenience can be immediately found, due to the fact that the measure load is very limited, and in any case smaller than the force which can be produced by the operator. The mark resulting on the piece under test is, therefore, imperceptible, particularly when the measurement is made on hard material.

Another important inconvenience is due to the fact that, being the measure load applied for a certain time, it is necessary to hold the equipment very firmly in position during this time, in order to avoid a possible mark deformation and consequently altered measures. This is very difficult to obtain, particularly in the case of equipments devoid of supporting bases as those used to measure pieces of reduced dimensions, or when the measures are made in difficult points where the meter is kept in the most strange positions, sometimes remarkably inclined with respect to the vertical.

The present invention intends to provide a hand-operated hardness meter where the above mentioned inconveniences are eliminated by the application of a force greater than the human one and moreover so instantaneous in its action as to render completely neglegible, in the very short period of load application, any oscillating movement of the penetrating pin axis, thus ensuring a sharp mark and a precise measure.

The meter of the present invention is characterized by the fact that between the mobile structure, kept moving by the operator's hands, and the rod of the penetrating pin is interposed a special device capable of applying on such rod an instantaneous force which acts as measure load independently of the force exerted by the operator. Moreover, such device weakens the reaction forces which, otherwise, would unload themselves over this mobile structure. The entire assembly is so arranged that the mobile structure displacement is used both to indicate the pre-load position of the penetrating pin (comprising, is desired, the equipment resetting) and to control the device in order to apply the instantaneous force as measure load.

The invention, presented in the following in form of an example, not at all limiting other possible embodiments, is illustrated in the next pages, with reference to the enclosed drawings, where:

Figure 9:
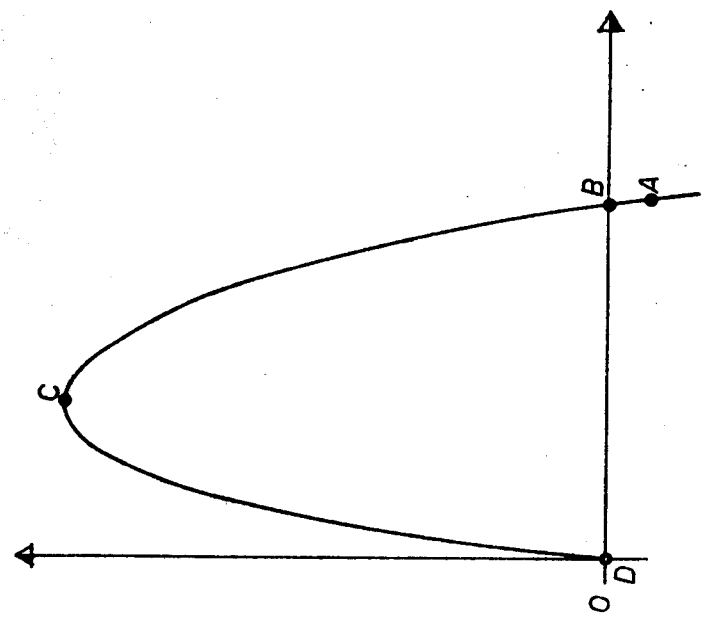

FIG. 9 presents a diagram of the variation of the load during the device release indicated in FIGS. 3 to 6.

Figure 1:
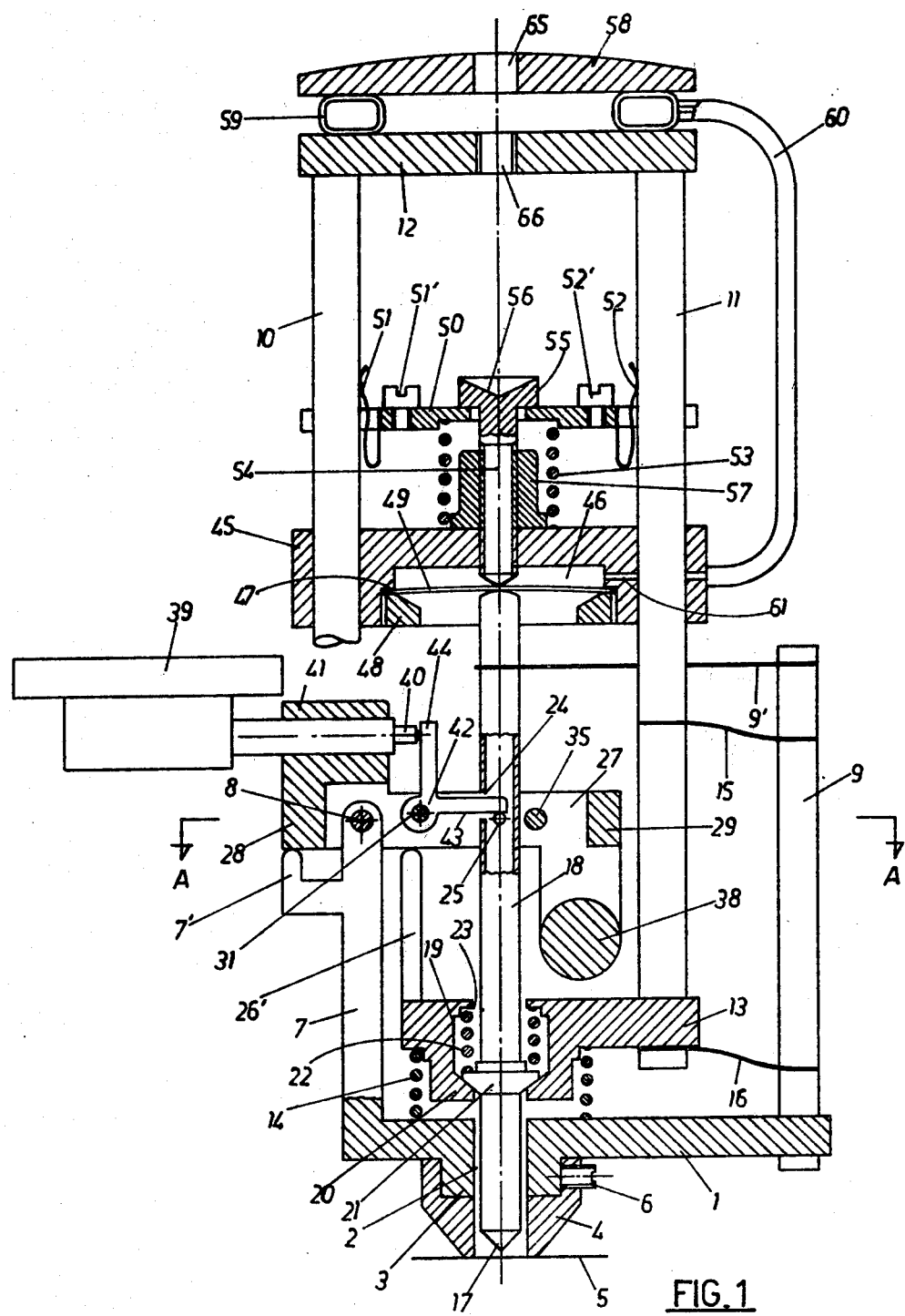
FIG. 1 is a view in elevation and in section of the hardness meter.
Figure 2:
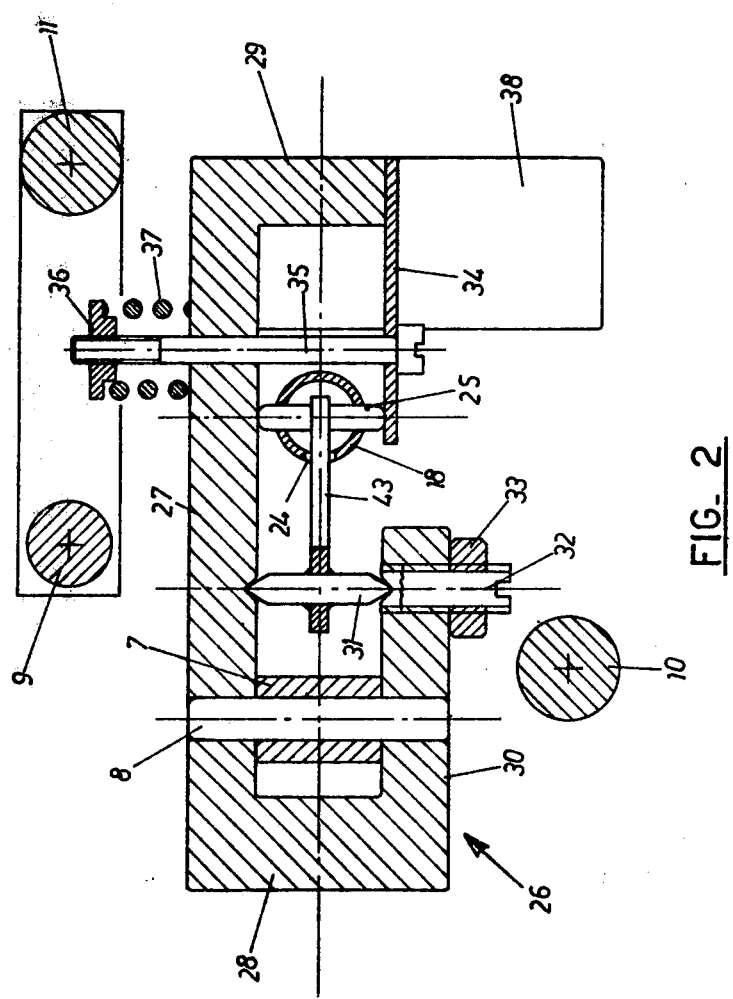
FIG. 2 is, in enlarged scale, a plane section according to line A—A of FIG. 1.

With reference to FIGS. 1 and 2, the hardness meter illustrated in the present paper includes a lower fixed structure which, in fact, remains fixed during the equipment operation. This fixed structure is composed of a lower plate 1 provided with a vertical hole 2, around which extends a collar 3. Around collar 3 is placed a metal ring 4 which in its lower part forms the reference plane 5. This ring is fixed by a grain 6 and, in the example of FIG. 1, tapers towards the reference plane in such a way as to determine a limiting surface on the piece to be measured. Such limited supporting surface is useful Particularly when measures are to made on pieces of small dimensions.

Figure 7:
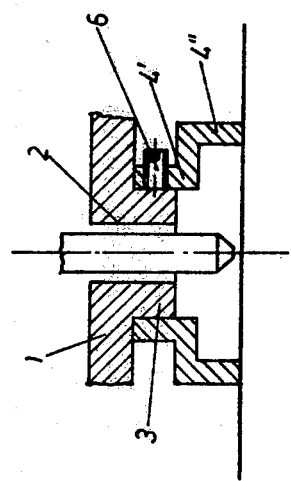
FIG. 7 is a variant of the metal ring which forms the reference plane.

However, the metal ring 4 can be rapidly changed with others, having larger supporting surfaces, as 4' in FIG. 7, which shows at the bottom a larger cylindrical wall 4" whose lower edge determines the reference plane, and, at the same time, a supporting surface remarkably larger. The change from one metal ring to the other can be made slackening grain 6.

The fixed structure is completed by a vertical arm 7 rigid with plate 1 and provided at its top extremity with a hole designed to receive exactly a hinge pin 8, protruding from both sides of arm 7. Also part of the fixed structure is a short column 9, which in FIG. 1 is indicated on the right side of the equipment, but only for ease of drawing; in reality it assumes the position indicated in FIG. 2.

The hardness meter also includes a mobile structure composed of two vertical columns 10 and 11, rigidly connected by a superior plate 12 and a lower plate 13 placed immediately above plate 1. When the equipment is at rest, plate 13 is kept at distance from plate 1 by a spacing h which constitutes the maximum excursion of the mobile structure with respect to the fixed one when the equipment is operated. The spacing h is determined by a spring 14 whose force is larger than the weight of the mobile structure plus the other organs supported by the structure itself which will be described later.

Naturally the mobile structure is properly guided in order to execute a displacement parallel to the axis of the penetrating pin. Means to achieve such precise movement may be of any type known in the technique of hardness meters. In the case of FIG. 1, for instance, column 11 is guided by two elastic sheets 15 and 16 which are parallel and rigidly connected both to the same column 11 and to fixed column 9, thus forming a sort of articulated parallelogram which insures in any case the axial trimming during the displacement of the mobile structure and, considering the limitation of the displacement itself, makes it neglegible the lateral displacement.

The penetrating pin 17 is carried by a rod 18 parallel to columns 10 and 11 and axially guided by an elastic sheet 9' connected between the rod itself and column 9. Rod 18 penetrates axially in hole 2 and crosses plate 13 which is provided to this end with cavity 19, having at the bottom a conical seat 20 against which—at rest—lays a conical support 21 also carried by rod 18. This support is pushed against the conical seat by a spring 22 compressed between the support itself and a restriction 23 existing on top of cavity 19. The conical seat 20 thus constitutes a sort of stopping gear which maintains exactly the position of the penetrating pin at a distance from the reference plane which is less than spacing h when plate 13, at rest, assumes this distance from plate 1.

Rod 18, at least for a certain portion, is tubular in shape and is provided on one side with a vertical split 24. Moreover, it is crossed in this position by a horizontal pin 25 which is at 90° with respect to the axial plane of split 24.

Pin 8, carried by arm 7, constitutes the fulcrum of a strong balancer 26 which, backside, is delimited by a continuous, vertical wall 27 and at its extremities is delimited by the opposite walls 28 and 29. On its left side such balancer presents a vertical wall 30 extending to about a half of the continuous wall 27.

As can be better seen in FIG. 2, walls 27 and 30 are provided with holes designed to receive respectively the extremities of pin 8. Between these walls is also kept a pin 31 (whose extremities are sharp-pointed) which settles in conical seats, one on wall 27 and the other on a grain 32. Such grain 32 is adjustable, in order to eliminate the slack of pin 31, and can be blocked in the registered position by a nut 33.

On the right side the balancer is provided with a flexible wall 34 opposed to the continuous wall 27, so that, between wall 27 and wall 34, pin 25 can be pressed axially. Axial pressure on pin 25 is regulated by a screw 35 which crosses walls 34 and 27 and outside this last wall is provided with a nut 36 acting on a spring 37. Pressure over pin 25 is adjusted in such a way as to permit the pin to run-with a certain friction- with its extremities suitably rounded, along walls 27 and 34, thus allowing to rod 18 the possibility of moving axially.

On its right extremity, balancer 26 is provided with a weight 38, while on the left extremity there is a comparator 39 mounted in cantilever, so that its probe 40 Protrudes from the inside of an increased thickness 41; the whole system is so arranged as to remain in equilibrium with respect to fulcrum 8.

Over pin 31 is articulated a small square element 42, an arm 43 of which penetrates split 24 going to lay on pin 25, while the other arm leans against the extremity of probe 40. The spring working on the probe, not visible in the figure although being part of the comparator, guarantees the contact of arms 43 and 44 respectively with pin 25 and probe 40, so that all movements of rod 18 with respect to the balancer are transmitted to probe 40.

Arms 43 and 44 are indicated in FIG. 1 as having the same length, but it is also possible that arm 44 be longer than arm 43 so that an amplified movement can be transmitted to the probe.

When at rest, balance 26 is maintained fixed by an arm 26', carried by the mobile plate 13 which brings it against a vertical stop 7' carried by rod 7, so that it is prevented from any oscillation in both directions.

On columns 10 and 11, above balance 26, is mounted a running inertial mass 45 which may run without slack along the same columns.

The inertial mass 45 is provided with a median cavity 46, having cylindrical lateral walls, which at its bottom is threaded down to ledge 47. A threaded ring 48 is engaged in the threading of cavity 46 in such a way as to tighten, between itself and ledge 47, the peripheral edge of a spring 49 made up of elastic steel and having the shape of a disc curved as a cover cap. This spring under an axial push may elastically react from one side to the other of the plane defined by the periferic edge. In the case of FIG. 1 the spring is shown in the "armed" position, with a limited deformation (as will be better explained later) so that, when it is released to the position presenting the convexity downward, it can apply all the generated force against the superior extremity of rod 18.

Above the inertial mass 45 is placed a breastband 50 provided with means capable of exerting a friction against columns 10 and 11. In FIG. 1 these are represented in a simplified version by two elastic sheets 51 and 52 fixed by screws 51' and 52 to the breastband and folded in such a way as to press against the respective columns, so that any movement of the breastband 50 along the same columns is breaked. Sheets 51 and 52 however, can be substituted by other means of friction capable to provide the same resistance Between breastband 50 and the inertial mass 45 is placed an helicoidal spring 53 whose force is smaller than the friction resistance of the elastic sheets 51 and 52.

A screw 54 going through a loose hole of breastband 50 descending to engage a threaded hole of the inertial mass 45, reaches with its extremity the cavity 46. This screw is adjustable so that the above extremity can restrain the working limits of spring 49 in order to make it possible the release of such spring by whatever limited force desired.

When screw 54 is in the above mentioned position its head 55 is laying on breastband 50, thus determining the loading of spring 53. This head 55 is also provided with a conical cavity 56 coaxial to the screw axis.

It must be underlined that the hole of breastband 50 and the threaded hole of the inertial mass 45 are coaxial with rod 18 so that screw 54 is also coaxial with this rod.

When screw 54 has been positioned as above, it remains blocked by a nut 57 and constitutes, together with the inertial mass 49, a rigid set which premits a free movement of such mass towards the breastband in contrast to spring 53, for a length determined by the distance of nut 57 from the breastband itself and for a maximum spacing determined by the contact of screw head 55 with ths same breastband.

Above plate 12 of the mobile structure a second plate 58 is provided, which is designed to receive the manual push of the operator during the measurement. Such plate 58 is kept at a distance from plate 12 by a toroidal, hollow body made up of yielding material, such as rubber. Starting from that body, a flexible tube 60 reaches a radial hole 61 in mass 45, which permits communication of this tube with cavity 46 delimited by the horizontal wall of this mass and by spring 49.

A fluid, preferably air, fills up the toroidal body 59, the flexible tube 60 and the cavity 46, so that a crushing impressed to toroidak body 59 determines a pressure increase which is transmitted to cavity 46, giving to sheet 49, when loaded, a thrust sufficient to release it on the opposite position.

The equipment works in the following way: initially the mobile structure is raised, so that plate 13 is at distance h from plate 1. Rod 18 is supported by conical seat 20, so that point 17 of the penetrating pin is kept at distance from the reference plane by a spacing smaller than h, balancer 26 is kept by arm 26' and by stop 7'. Spring 49 is loaded and mass 45 is lowered so that such spring touches the upper extremity of rod 18.

The operator, after having placed the instrument on the piece to be measured, begins to press on the upper plate 58, thus causing the progressive lowering of the mobile structure. During this lowering phase the penetrating pin 17 enters in contact with the piece to be measured, thus causing the stop of rod 18 and then the stop of mass 45, while breastband 50 continues its movement together with columns 10 and 11, because spring 53, although in the Process of loading, offers a thrust lower than the friction resistance of sheets 51 and 52.

During the lowering of the rod, pin 25, carried by the rod itself, originates by friction a rotation of balancer 26, without giving rise to any relative displacement of the small square element 42, so that no movement is recorded by the comparator.

As soon as rod 18 stops support 21 is separated from its seat 20, so that the rod remains subjected to spring 22. When plate 13 enters in contact with fixed plate 1, the mobile structure stops. In this position rod 18 will be subjected to spring 22 and spring 53, which therefore supply the pre-load to the penetrating pin. Continuing the push on plate 58 by the operator, the crushing of toroidal body 59 is obtained, thus determining an increase of the fluid pressure in cavity 46 which in turn produces a thrust on spring 49 and then its release.

The successive phases of the spring release are illustrated in FIGS. from 3 to 6.

Figure 3:
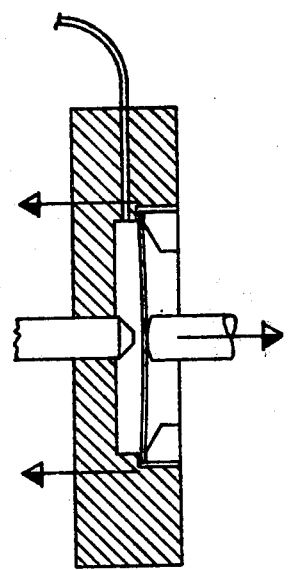
FIGS. 3 to 6 show the successive phases of the application of the instantaneous force with the equipment presented as an example in the figures.

Position A in FIG. 3 is the initial one, corresponding to

FIG. 1, when pressure on the fluid in cavity 46 is generated.

Figure 4:
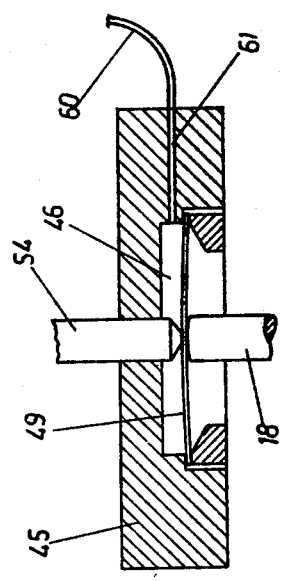

Position B in FIG. 4 is the one in which spring 45 has started its release deformation to the median plane.

Figure 5:
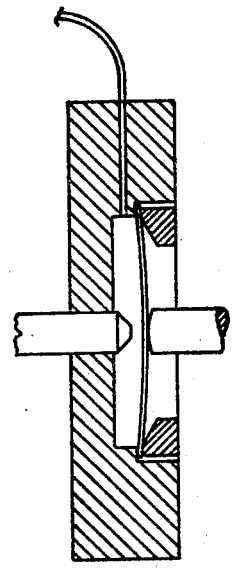

Position C in FIG. 5 is the one in which, after passing the median plane, the spring reaches an intermediate deformation and provides the maximum load.

Figure 6:
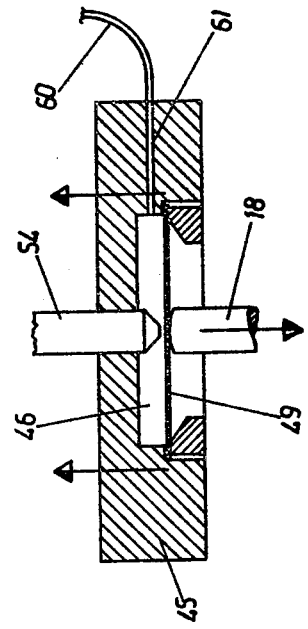

FIG. 6 shows the final position D of the spring at the end of the release.

With reference to FIG. 1 and to FIGS. 4, 5 and 6 it can be noted how the disc spring 49 presses constantly on rod 18 which offers a constraint moving for a very short distance equal to the depth of the mark left by the penetrating pin on the piece under test. Consequently almost the entire energy, provided by the spring release is discharged, by reaction, on the inertial mass 45, which is thrown upward with a remarkable acceleration having a duration equal to the one of the spring release. The duration of the load due to the spring release and acting on rod 18 is directly proportional to the weight of the inertial mass. Therefore it is preferable that such mass be of limited weight, in order to obtain a load practically instantaneous and independent- quantitatively - from the force applied by the operator and also much higher than this force.

Coming back to FIG. 1, it can be seen that mass 45, when thrown upward, covers freely the distance between nut 57 and breastband 50, being opposed only by spring 53, whose push is neglegible with respect to the kinetic energy of the mass itself. At the end of this distance, mass 45 impacts against breastband 50 which is dragged in the movement, while at the same time the whole moving system is braked by the resistance of friction sheets 51 and 52, so that after a certain distance along columns 10 and 11, the entire system is stopped. It is evident that, with such an arrangement, the braking action prevents the kinetic energy of mass 45 from discharging itself against the operator hand, which, therefore, will have to bear only the friction force, considerably lower.

FIG. 9 shows the diagram of loading as a function of the deformations of spring 49. From the diagram points A, B, C and D are evident, corresponding to positions of FIGS. 3, 4, 5 and 6 respectively.

It is possible to see that point A corresponds to the "armament" of the spring which is determined by the extremity of screw 54 and offers a limited negative load. Such load must be overcome to induce the spring release.

Point B is the position assumed by the spring at the moment it overcomes the median plane having zero load.

Point C indicates the position of maximum spring loading, corresponding to about the intermediate deformation between the maximum downward convexity (point D) and the median plane (point B).

Point D indicates the maximum deformation with downward convexity, when the spring supplies a zero load.

The trend from the origin to the right side of the abscissa axis shows the "armament" phase executed as specified in the following, while the trend from point A towards point D shows the discharge phase of the spring when it applies the measure load on rod 18, as previously explained.

Coming back to FIG. 1, the axial displacement of rod 18, due to the instantaneous measure load impressed by spring 49, will also be instantaneous. In these conditions the inertia offered by balancer 26 is so high to oppose such displacement, so that rod 18 and pin 25 move relatively to the balancer because of the sliding by friction of the rounded pin extremities, along walls 27 and 34. This relative displacement will be exactly followed by the small square element 42 and by probe 40 thus transmitting to the comparator the depth measure of the penetrating pin and therefore the hardness value of the measured piece.

It must be noted, from the preceding explanation, that the small oscillations caused by the operator during the measurement operation, particularly when the support base is small, are not recorded by the comparator because the balancer always follows the rod of the penetrating pin thanks to the adjustable friction of pin 25 to walls 27 and 34 of the same balancer.

Moreover, due to the high rapidity of the measure load application and therefore to the sudden displacement of the rod, which is the only one recorded by the comparator, possible slow oscillations are not perceived.

At the end of the test it will be necessary to execute the rearmament of spring 49 and the readjustment of pin 25 relatively to balancer 26. The readjustment of pin 25 takes place automatically after the withdrawal of the external loads from the equipment. In these conditions spring 14 tends to bring the mobile structure back to the rest position shown in FIG. 1. As soon as this plate 13 rises, it engages first stopper 21 of rod 18 which is carried upward together with pin 25.

Pin 25, in turn, carries balancer 26, turning it anti-clockwise until it leans on register 7' and stops. Continuing the upward movement of rod 18, pin 25 will be induced to slide with respect to walls 27 and 34 going back to the initial position when the mobile structure stops in the rest position and arm 26' is in contact with the same balancer.

Figure 8:
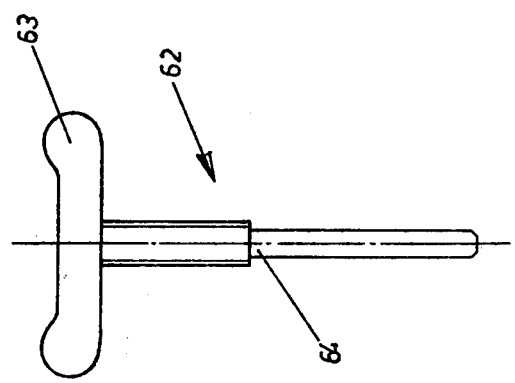
FIG. 8 shows a key used for loading or arming the device which is employed to apply the instantaneous force.

In order to rearm spring 49, the key 62 illustrated in FIG. 8 is used. Such key is provided with a head 63 shaped as a butterfly turning knob, which in its first portion is threaded and for the remaining part is smooth.

The key is inserted in a first loose hole 65, existing on plate 58 axially with rod 18 and screwed in the threaded hole 66 of plate 12, also axially with rod 18. The initial insertion brings the key extremity to press into cavity 56 of the screw 54 head, which in turn pulshes downward 50, together with mass 45.

After a certain distance the key engages the threaded hole 66 and its axial displacement continues in form of screwing, with the possibility of obtaining a thrust sufficient to arm spring 49.

With spring 49 in the position of FIG. 6, screw 54 is moved downward carrying again the inertial mass 45, while rod 18 acts as a constraint to spring 49 which, therefore, will be deformed until it overcomes the position of the median plane and the deformation will be with the convexity upward, limited by screw 54 extremity.

In the example described the device capable to impress an instantaneous force is constituted by the disc spring 49 and inertial mass 45.

It is foreseen, however, the employment of another device also suitable to provide an instantaneous force. Such device, for example, may be a pneumatic one, whose cylinder properly constitutes the inertial mass and can move along columns 10 and 11, while the piston, instead of spring 49, is capable to act on rod 18. In this embodiment the flexible tube 60, adequately lengthened, is connected to a pressurized source of air or gas, the feeding of the cylinder being controlled by a suitable electric tube which is excited after the application of the pre-load and is disexcited after the measure, when the mobile structure is returning upward.

According to a further embodiment, the device can be constituted by an electromagnet whose iron armature forms the inertial mass guided along columns 10 and 11 and whose core is in place of spring 49. Also in this case the electromagnet excitation will take place soon after the pre-load application and the disexcitation at the end of the measure.

Naturally any other device capable of providing an instantaneous force axially to rod 18 and arranged in such a way as not to discharge the reaction force on the mobile structure and on the operator's hands can be utilized within the framework of the present invention. Moreover, the braking of the inertial mass can also be made with pneumatic or electromagnetic means. Finally, electronic means may be used to measure rapidly the penetration depth.

I claim:

1. Apparatus for measuring the hardness of a material, comprising: a stationary-frame structure having an axis; means for penetrating the material, the penetrating means being movable in an axial direction with respect to the stationary frame structure and having one end provided to penetrate the material and another end; means for applying a penetrating force onto the penetrating means and including a first member being continuously in contact with the other end of the penetrating means and movable between a first position in which no force is exerted on the other end and a second position in which the penetrating force is exerted thereon, and a second member constituting an inertia mass which cooperates with the first member in such a manner that upon movement of the first member into the second position, the penetrating means is caused to penetrate the material while the inertia mass is simultaneously accelerated in opposite direction to the movement of the penetrating means; means for driving the first member from the first into the second position; and means for measuring the hardness of the material in dependance on the penetration of the penetrating means into the material.

2. Apparatus as defined in claim 1; and further comprising means for decelerating the movement of the second member after exertion of the penetration force onto the penetrating means.

3. Apparatus as defined in claim 1, wherein the first member is a spring having one surface with a centrical area being in contact with the other end of the penetrating means, and another surface with a peripheral abutting the second member so that a cavity is provided between the spring and the second member wherein upon movement of the spring from the first position to the second position, the penetrating means is accelerated towards the material and the second member is accelerated in opposite direction away from the material.

4. Apparatus as defined in claim 3, wherein the spring is a convex disc movable from one convexity constituting the first position in which the spring rests on the other end of the penetrating means without applying any force thereon, to the other convexity constituting the second position in which the spring exerts the penetrating force onto the other end of the penetrating means.

5. Apparatus as defined in claim 4, wherein the spring is of elastic steel.

6. Apparatus as defined in claim 3, wherein the driving means includes an upper plate and a hollow element containing a fluid and cooperating with the upper plate so that upon exertion of a predetermined outside force on the upper plate, the fluid is forced into the cavity thereby moving the spring from the first position into the second position so as to exert the penetrating force onto the other end of the penetrating means.

7. Apparatus as defined in claim 2; and further comprising two support columns extending parallel to each other in axial direction, the second member being movably arranged along the columns wherein the decelerating means including a transverse member movably arranged along the columns and located above the second member, and at least one friction member connected to the transverse member and provided to press against the associated column so as to decelerate the movement of the second member when the penetrating force is exerted by the first member.

8. Apparatus as defined in claim 1, wherein the measuring means includes an inertial component frictionally connected to the penetrating means so as to prevent a relative movement there between when the penetrating means is moved in the axial direction by a force smaller than the penetrating force and to allow a relative movement when the penetrating means is accelerated towards the material upon exertion of the penetrating force by the first member.

9. Apparatus as defined in claim 8, wherein the measuring means further comprises a comparator connected to the inertial component and cooperating with the latter so as to register the relative movement between the penetrating means and the inertial component for measuring the hardness of the material in dependance on the penetration of the penetrating means into the material.

10. Apparatus as defined in claim 9, wherein the measuring means further comprises a counter-weight to the comparator connected to the inertial component so as to provide the measuring means in an equilibrium with respect to the housing.

* * * * *